(12) United States Patent
Laufer

(10) Patent No.: US 7,455,670 B2
(45) Date of Patent: Nov. 25, 2008

(54) SYSTEM AND METHOD FOR THE TREATMENT OF HEART TISSUE

(75) Inventor: Michael D. Laufer, Menlo Park, CA (US)

(73) Assignee: Co-Repair, Inc., Sunnyvale, CA (US)

( * ) Notice: Subject to any disclaimer, the term of this patent is extended or adjusted under 35 U.S.C. 154(b) by 381 days.

(21) Appl. No.: 11/035,657

(22) Filed: Jan. 14, 2005

(65) Prior Publication Data

US 2006/0161229 A1     Jul. 20, 2006

(51) Int. Cl.
A61B 18/18     (2006.01)
(52) U.S. Cl. .......................................... 606/38; 606/41
(58) Field of Classification Search ............. 606/27–52
See application file for complete search history.

(56) References Cited

U.S. PATENT DOCUMENTS

| | | | |
|---|---|---|---|
| 4,697,595 A | 10/1987 | Breyer et al. | |
| 4,709,698 A * | 12/1987 | Johnston et al. | 606/41 |
| 5,156,151 A | 10/1992 | Imran | |
| 5,324,284 A | 6/1994 | Imran | |
| 5,334,193 A | 8/1994 | Nardella | |
| 5,409,000 A | 4/1995 | Imran | |
| 5,466,255 A * | 11/1995 | Franchi | 607/128 |
| 5,471,982 A * | 12/1995 | Edwards et al. | 600/374 |
| 5,500,012 A | 3/1996 | Brucker et al. | |
| 5,529,067 A | 6/1996 | Larsen et al. | |
| 5,606,974 A | 3/1997 | Castellano et al. | |
| 5,688,267 A | 11/1997 | Panescu et al. | |
| 5,693,078 A | 12/1997 | Desai et al. | |
| 5,697,882 A | 12/1997 | Eggers et al. | |
| 5,735,846 A | 4/1998 | Panescu et al. | |
| 5,827,268 A | 10/1998 | Laufer | |
| 5,904,711 A * | 5/1999 | Flom et al. | 607/129 |
| 5,916,213 A | 6/1999 | Haissaguerre et al. | |
| 5,928,224 A | 7/1999 | Laufer | |
| 5,989,284 A | 11/1999 | Laufer | |
| 6,004,316 A * | 12/1999 | Laufer | 606/28 |
| 6,029,091 A | 2/2000 | Da la-Rama et al. | |
| 6,030,379 A | 2/2000 | Panescu et al. | |
| 6,059,778 A | 5/2000 | Sherman | |
| 6,071,303 A | 6/2000 | Laufer | |
| 6,163,716 A * | 12/2000 | Edwards et al. | 600/374 |
| 6,283,988 B1 * | 9/2001 | Laufer et al. | 607/96 |
| 6,315,778 B1 * | 11/2001 | Gambale et al. | 606/41 |
| 6,463,332 B1 * | 10/2002 | Aldrich | 607/101 |
| 6,558,382 B2 | 5/2003 | Jahns et al. | |
| 6,577,902 B1 | 6/2003 | Laufer et al. | |
| 6,584,360 B2 | 6/2003 | Francischelli et al. | |
| 6,616,657 B2 | 9/2003 | Simpson et al. | |
| 6,635,056 B2 | 10/2003 | Kadhiresan et al. | |
| 6,669,687 B1 | 12/2003 | Saadat | |
| 6,697,676 B2 * | 2/2004 | Dahl et al. | 607/126 |
| 6,711,429 B1 | 3/2004 | Gilboa et al. | |
| 6,723,092 B2 | 4/2004 | Brown et al. | |
| 6,752,804 B2 | 6/2004 | Simpson et al. | |

(Continued)

*Primary Examiner*—Henry M Johnson, III
(74) *Attorney, Agent, or Firm*—Thelen LLP

(57) ABSTRACT

A device is disclosed for locating and treating an infarct scar in a heart. The device includes a catheter, a collapsible heater and energizing means connected to the collapsible heater for energizing the collapsible heater to raise the temperature of the infarct scar to a temperature sufficient to reduce the surface area of the infarct scar.

15 Claims, 11 Drawing Sheets

U.S. PATENT DOCUMENTS

| | | |
|---|---|---|
| 6,855,144 B2 | 2/2005 | Lesh |
| 7,041,098 B2 * | 5/2006 | Farley et al. .................. 606/41 |
| 2002/0151949 A1 * | 10/2002 | Dahl et al. .................. 607/126 |
| 2002/0198522 A1 * | 12/2002 | Kordis ......................... 606/41 |
| 2003/0018358 A1 * | 1/2003 | Saadat ....................... 606/232 |
| 2003/0050685 A1 | 3/2003 | Nikolic et al. |
| 2003/0191511 A1 | 10/2003 | Laufer et al. |
| 2005/0096647 A1 * | 5/2005 | Steinke et al. ................. 606/41 |
| 2006/0074410 A1 * | 4/2006 | Malecki et al. ............... 606/32 |

* cited by examiner

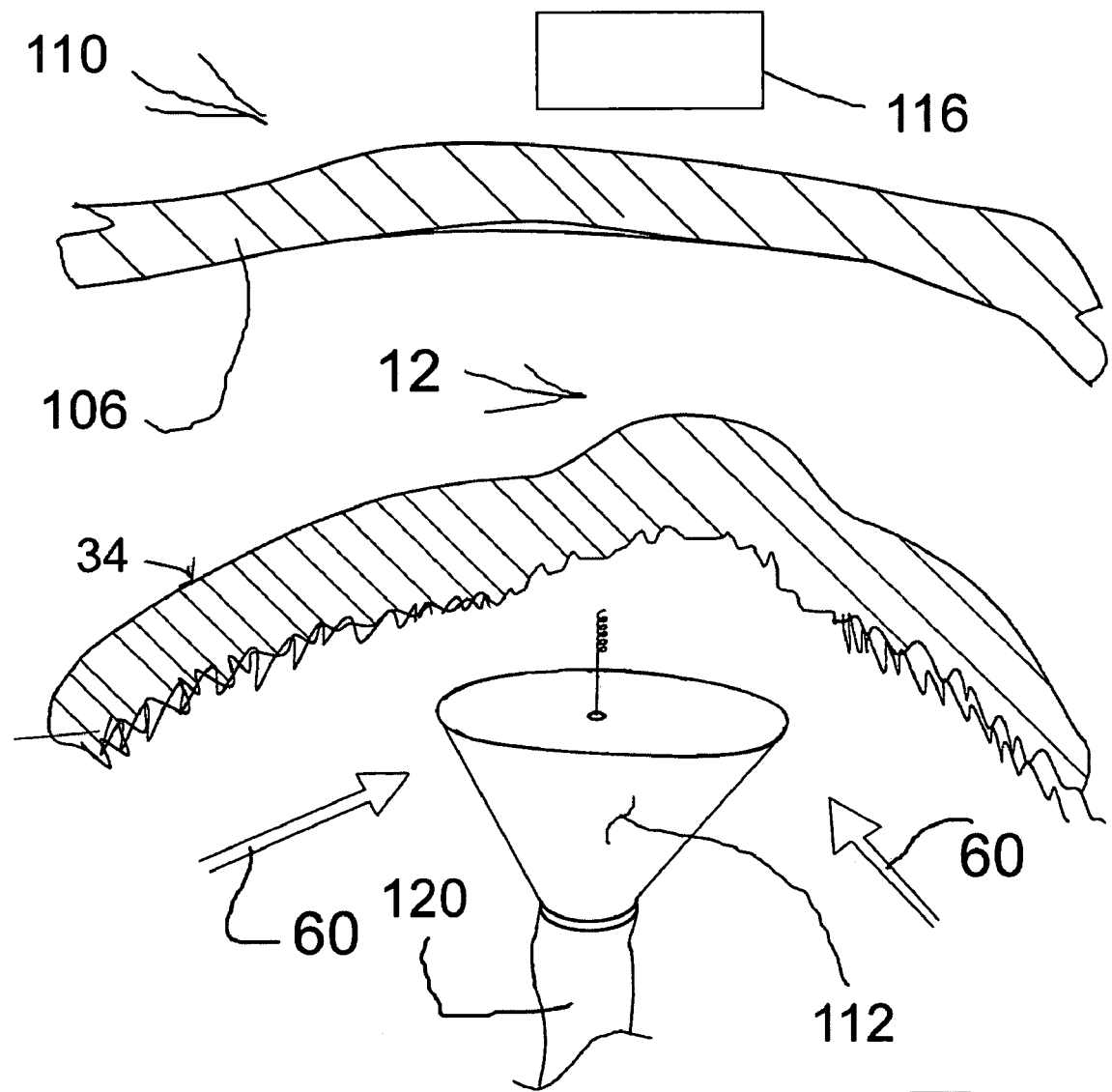
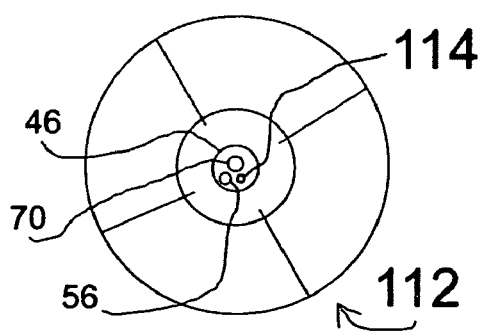
Fig. 7a
Fig. 7b

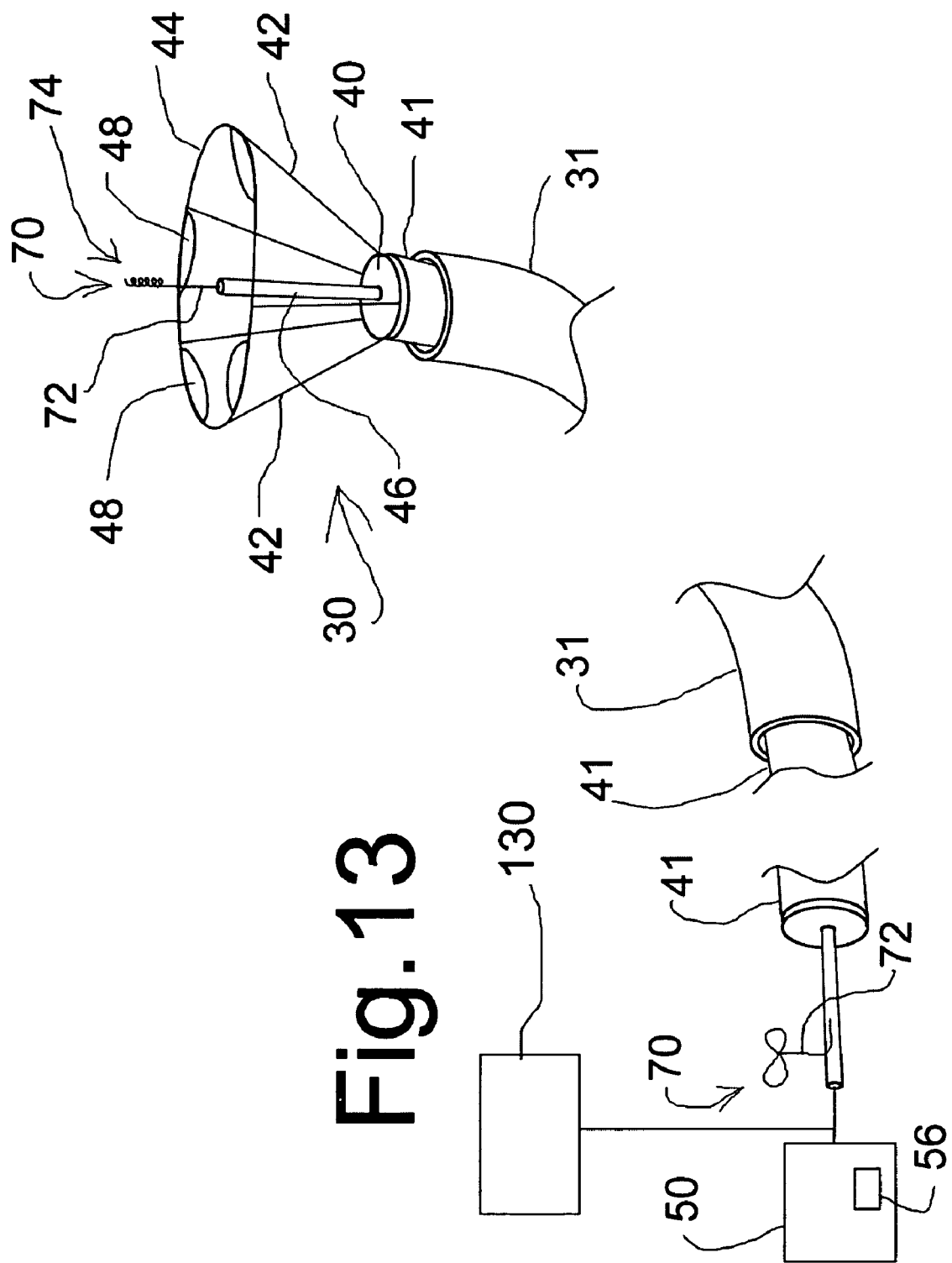

SYSTEM AND METHOD FOR THE TREATMENT OF HEART TISSUE

FIELD OF THE INVENTION

The present invention is related generally to the medical treatment of the heart, including modification of heart tissue for the treatment of myocardial infarction.

BACKGROUND OF THE INVENTION

As is well known, the heart has four chambers for receiving and pumping blood to various parts of the body. During normal operation of the heart, oxygen-poor blood returning from the body enters the right atrium. The right atrium fills with blood and eventually contracts to expel the blood through the tricuspid valve to the right ventricle. Contraction of the right ventricle ejects the blood in a pulse-like manner into the pulmonary artery and each lung. The oxygenated blood leaves the lungs through the pulmonary veins and fills the left atrium. The left atrium fills with blood and eventually contracts to expel the blood through the mitral valve to the left ventricle. Contraction of the left ventricle forces blood through the aorta to eventually deliver the oxygenated blood to the rest of the body.

Myocardial infarction (i.e., heart attack) can result in congestive heart failure. Congestive heart failure is a condition wherein the heart can not pump enough blood. When patients have a heart attack, part of the circulation to the heart wall muscle is lost usually due to a blood clot which dislodges from a larger artery and obstructs a coronary artery. If the clot is not dissolved within about 3 to 4 hours, the muscle which lost its blood supply necroses and subsequently becomes a scar. The scarred muscle is not contractile, and therefore it does not contribute to the pumping ability of the heart. In addition, the scarred muscle is elastic (i.e., floppy) which further reduces the efficiency of the heart because a portion of the force created by the remaining healthy muscle bulges out the scarred tissue (i.e., ventricular aneurism) instead of pumping the blood out of the heart.

Congestive heart failure is generally treated with lots of rest, a low-salt diet, and medications such as A.C.E. inhibitors, digitalis, vasodilators and diuretics. In some myocardial infarction instances, the scarred muscle is cut out of the heart and the remaining portions of the heart are sutured (i.e., aneurismechtomy). In limited circumstances a heart transplant may be performed. The condition is always progressive and eventually results in patient death.

Collagen-containing tissue is ubiquitous in normal human body tissues. Collagen makes up a substantial portion of scar tissue, including cardiac scar tissue resulting from healing after a heart attack. Collagen demonstrates several unique characteristics not found in other tissues. Intermolecular cross links provide collagen-containing tissue with unique physical properties of high tensile strength and substantial elasticity. A property of collagen is that collagen fibers shorten when heated. This molecular response to temperature elevation is believed to be the result of rupture of the collagen stabilizing cross links and immediate contraction of the collagen fibers to about one-third of their original length. If heated to approximately 70 degrees Centigrade, the cross links will again form at the new dimension. If the collagen is heated above about 85 degrees Centigrade, the fibers will still shorten, but crosslinking will not occur, resulting in denaturation. The denatured collagen is quite expansile and relatively inelastic. In living tissue, denatured collagen is replaced by fibroblasts with organized fibers of collagen than can again be treated if necessary. Another property of collagen is that the caliber of the individual fibers increases greatly, over four fold, without changing the structural integrity of the connective tissue.

U.S. Pat. No. 6,071,303 teaches a device and method for treating infarct scar tissue of a mammalian heart by selectively heating the infarct scar to reduce the size of the scar tissue surface area, increase the cross-section of the scar tissue, stiffen the floppy portion of the scar tissue, reduce the ventricular systolic wall tension, and increase the overall pumping efficiency of the infarcted heart by eliminating the ventricular aneurism or dilated ventricle, if present. FIG. 1 illustrates an embodiment of the device taught in U.S. Pat. No. 6,071,303.

Referring to FIG. 1, there is illustrated a heart 10 having an infarcted region or portion 12. The infarcted portion 12 of the heart can be accessed with conventional open chest surgery. A positive electrode 14 and negative electrode 16 are applied externally to a portion of the infarcted portion 12 to induce resistive heating in the infarct scar in the desired treatment area 18 when energy is applied across the electrodes. Alternatively, the positive and negative electrodes can be inserted into the infarcted scar. The positive and negative electrodes function as a heating element as they are energized to raise the temperature of the scar in the desired treatment area 18 to a controlled temperature sufficient to reduce the surface area of the scar without ablating the scar tissue or damaging the healthy tissue surrounding the infarcted portion 12.

U.S. Pat. No. 6,071,303 also teaches other appliances for applying radiant energy or thermal energy, or to otherwise heat the infarcted tissue and reduce the area of the infarcted tissue. For example, as shown in FIG. 2 a radio-frequency generator 20 and heating element applicator 22 can be used. When the heating element 24 of the applicator 22 is positioned at the desired treatment site, the radio-frequency generator 20 is activated to provide suitable energy, preferably at a selected frequency in the range of 10 megahertz to 1000 megahertz, to heat the scar tissue to a temperature sufficient to reduce the surface area of the scar without ablating the scar tissue or damaging the healthy tissue surrounding the infarcted area 12.

It should be understood that the devices taught in U.S. Pat. No. 6,071,303 are located external to the heart. However, I have found that in certain circumstances it can be preferable to apply heat in the internal surface of the heart. For example, in some cases the scar tissue is more severe or larger or both, within the heart than on the surface. Also, the use of the devices taught in U.S. Pat. No. 6,071,303 can require conventional open chest surgery. However, in some cases it is desirable for the surgeon to gain access to the patient's heart by catheterization.

It is an object of the present invention to provide a means to apply heat to a patient's infarct scar using a device deployed by a catheterization procedure so that the device is located inside the heart.

It is another object of the present invention to provide a means to apply heat to a patient's infarct scar using a device located inside the heart to raise the temperature of the scar in the desired treatment area to a controlled temperature sufficient to reduce the surface area of the scar without ablating the scar tissue or damaging the healthy tissue surrounding the infarcted portion.

It is another object of the invention to provide a means to locate a patient's infarct scar.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings:

FIG. 7a is view of an alternative embodiment.

FIG. 7b is another view of the alternative embodiment of FIG. 7a.

FIG. 13 is a view of still another embodiment.

DETAILED DESCRIPTION

Embodiments of the present invention are described herein in the context of a system and method for treatment of infarcted heart tissue. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Turning to FIGS. 3-7, the first embodiment of the present invention includes a catheter 31 and a collapsible heater 30 attached to the distal end of the a flexible cable 41. The cable 41 is located in the lumen of the catheter 31 so that the cable 41 can slide therein.

Figure 6:
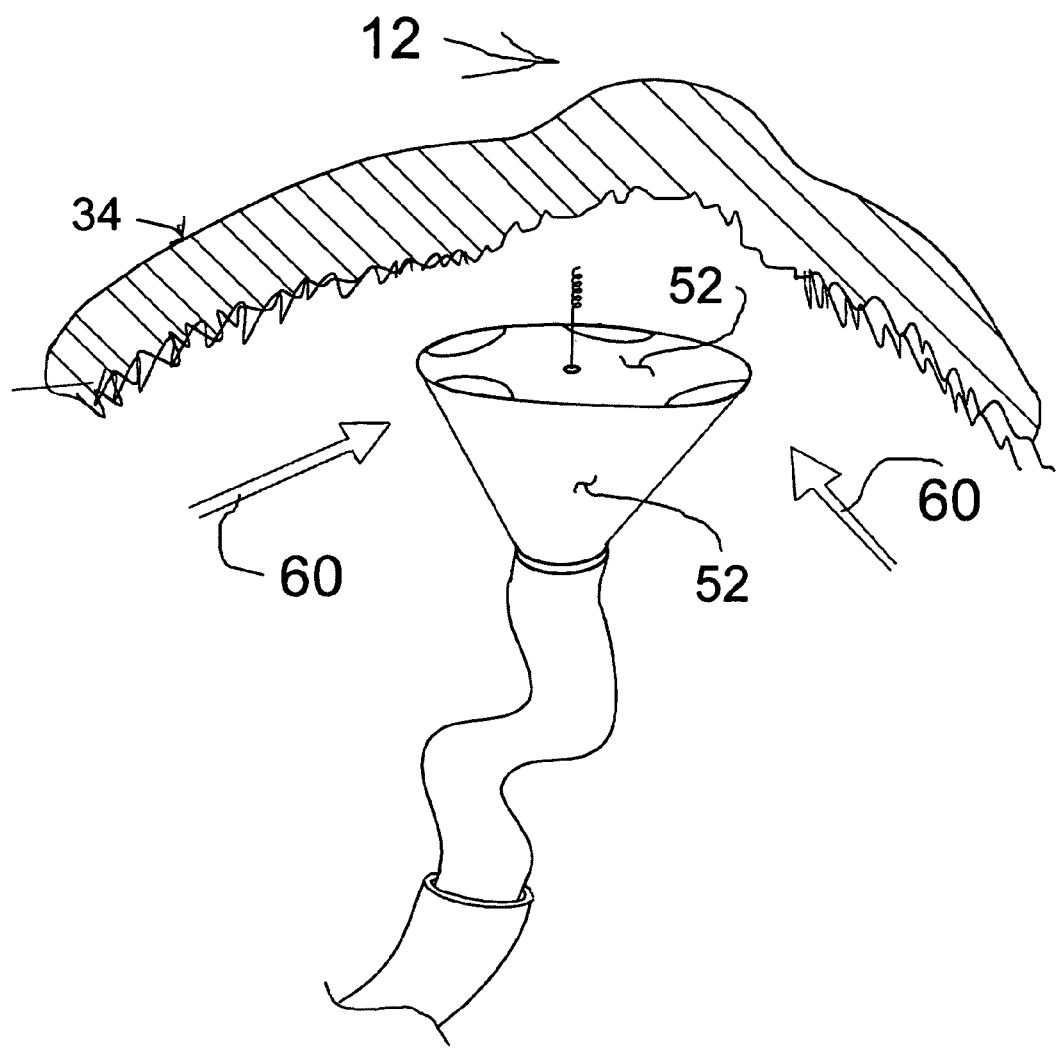
FIG. 6 is another view of the system of FIG. 3 illustrating its operation as the heart contracts.
Figure 7:
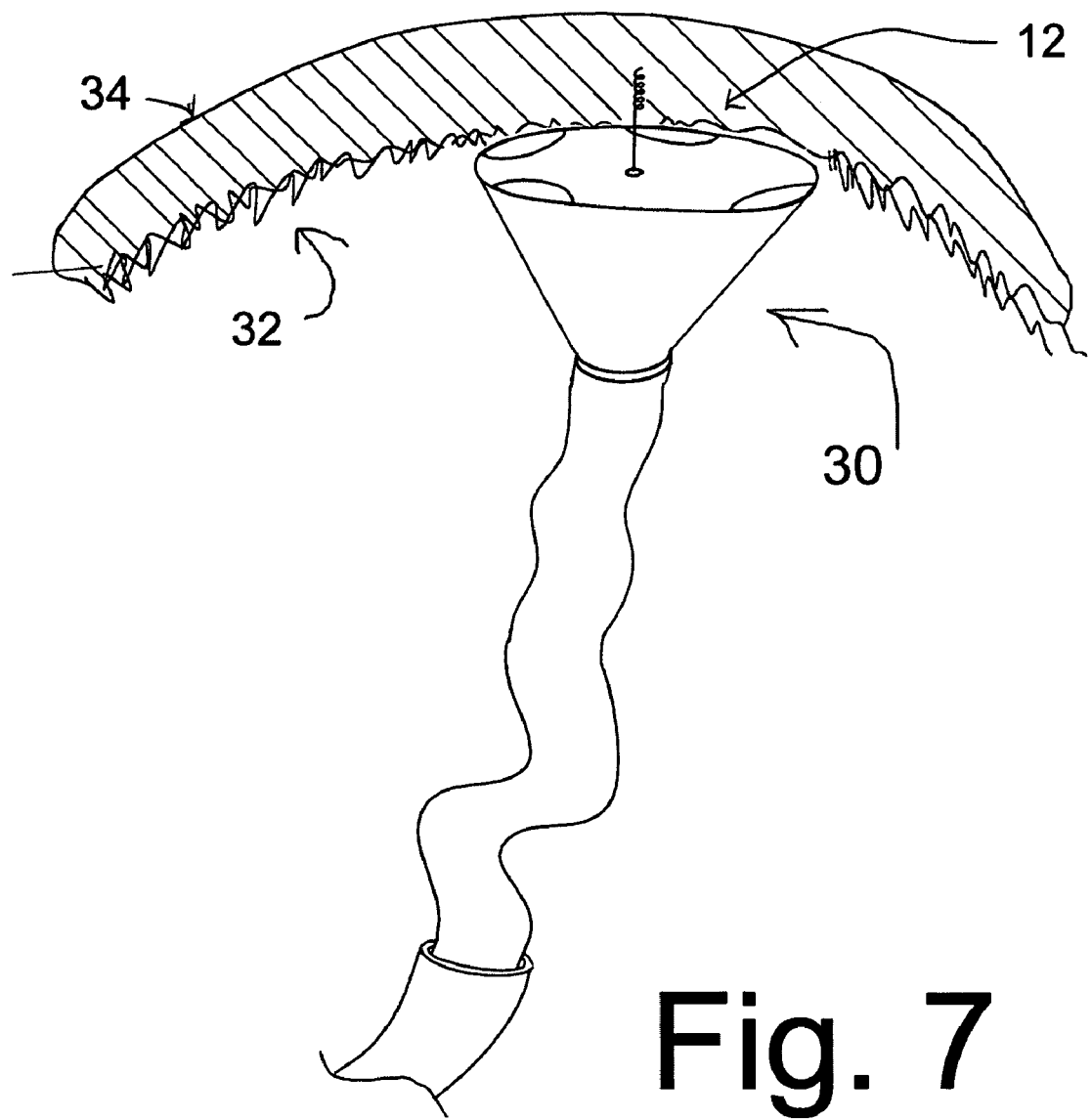
FIG. 7 is another view of the system of FIG. 3 illustrating its operation as the heart relaxes.

The collapsible heater 30 comprises a ring 40 mounted to the distal end of the flexible cable 41, and a plurality of struts 42 are mounted with their proximal ends affixed to the ring 40. The struts 42 are flexible and spring-like so that they can flex toward and away from the center axis of the ring 40. At the distal ends of the struts 42 a flexible wire 44 is mounted in a circular configuration to limit the outward motion of the distal ends of the struts 42. A center electrode 46 is located along the center axis of the ring 40, and a plurality of outside electrodes 48 are mounted to the wire 44. The center electrode 46 and outside electrodes 48 are electrically connected to a radio-frequency generator 50 that is located outside the patient's body. A mylar sheet 52 forms a bag-like structure which is located around the collapsible heater to completely enclose the struts 42, wire 44 and electrodes 46 and 48, and the proximal end of the mylar sheet 52 is connected to the ring 40. (The mylar sheet 52 is shown in FIGS. 6 and 7 but omitted from FIGS. 3 and 4 to permit the internal components to be seen.) Alternatively, the electrodes may be an integral part of the mylar sheet 52, with one configuration that the electrodes are printed in electrically-conductive ink on the mylar. Also, the mylar itself can act as a restraint on the struts 42, obviating the need for wire 44.

An attachment member 70 extends through the cable 41 and from the distal end of the collapsible heater 30. The attachment member 70 comprises a thin, flexible rod 72 which extends through a lumen in the cable 41 and through a lumen in the center electrode 46. A corkscrew-shaped connector 74 is located at the distal end of the rod 72, and a handle 76 is located at the proximal end of the rod 72 so that a user can rotate the handle 76 to cause the corkscrew-shaped connector 74 to rotate.

Figure 1:
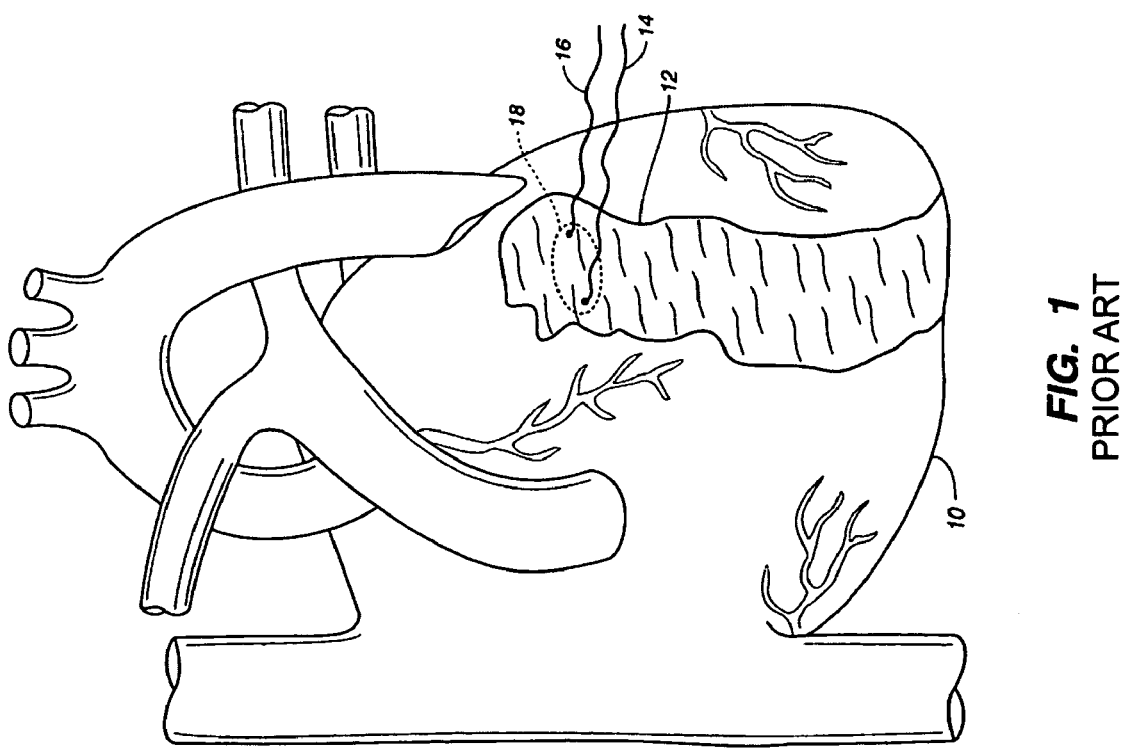
FIG. 1 is a view of a conventional system for the treatment of infarcted heart tissue.
Figure 2:
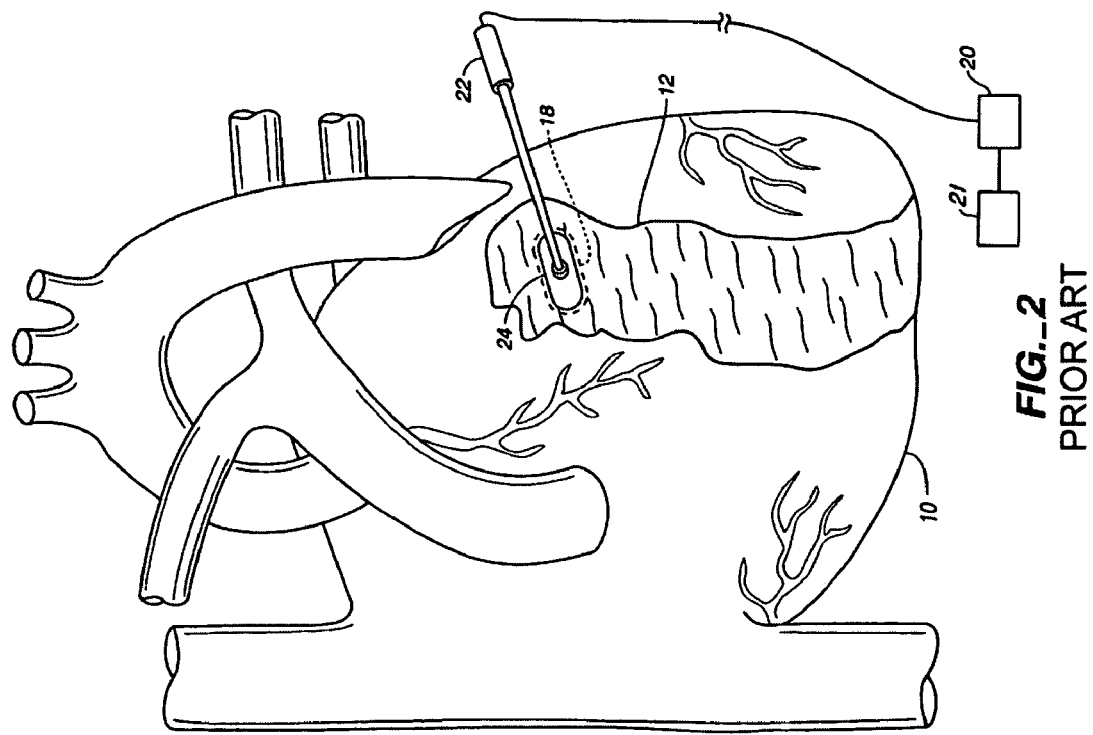
FIG. 2 is a view of another conventional system for the treatment of infarcted heart tissue.
Figure 3:
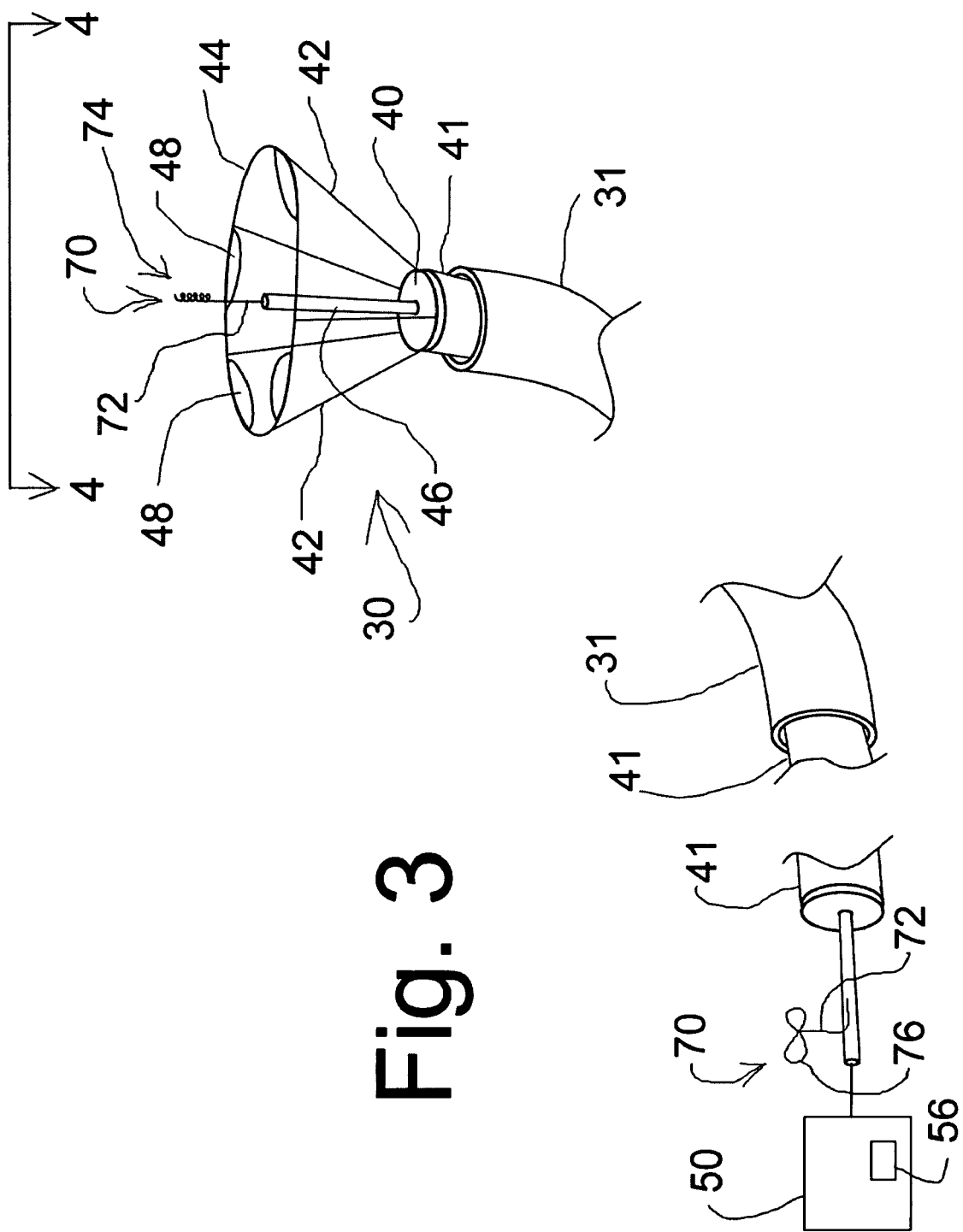
FIG. 3 is a view of a system for the treatment of infarcted heart tissue according to a preferred embodiment of the present invention, with portions removed for clarity and to show internal components.
Figure 4:
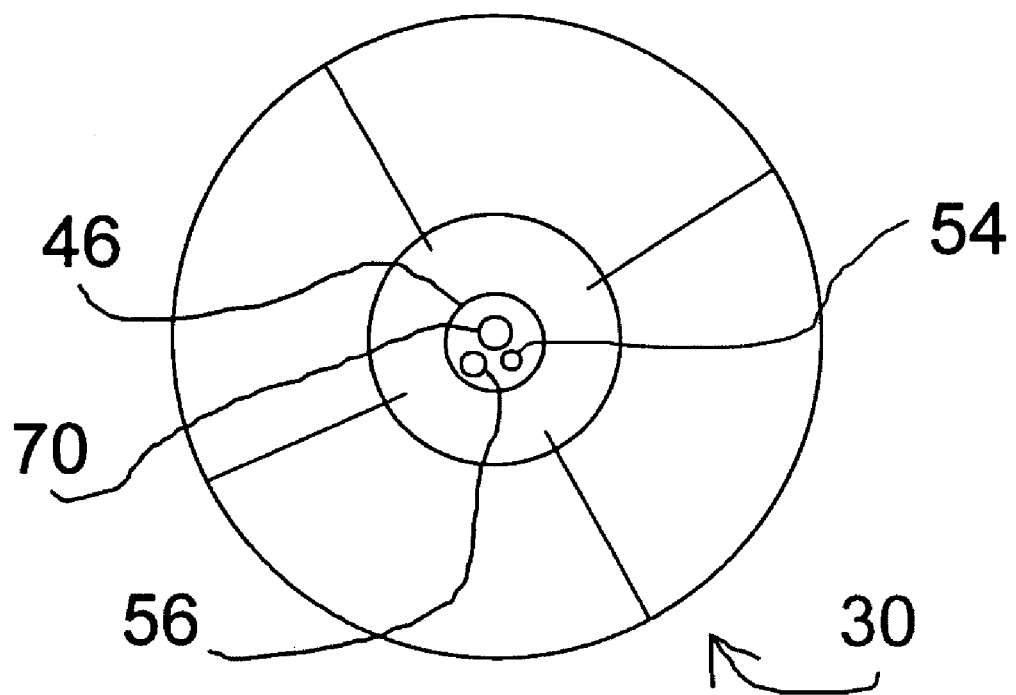
FIG. 4 is a view of the system shown in FIG. 3, taken along line 4-4 of FIG. 3
Figure 5:
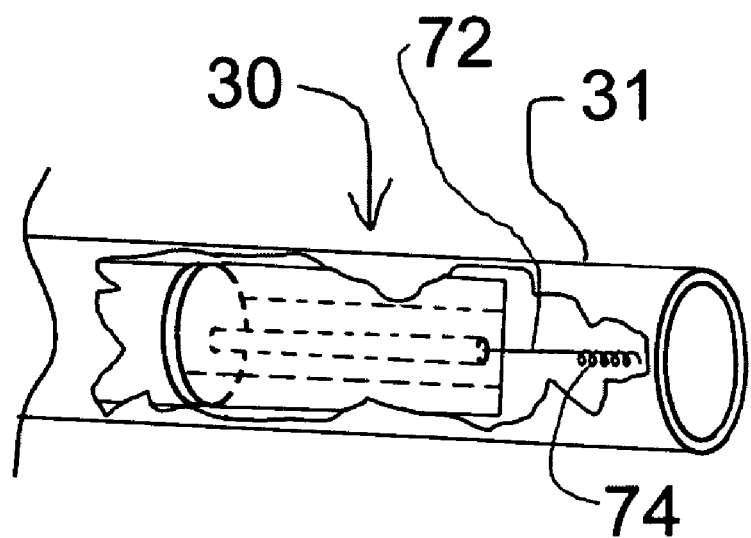
FIG. 5 is a view a portion of the system of FIG. 3 illustrating its operation.

To operate the device shown in FIGS. 3-7, first a physician introduces a catheter 31 into a patient so that the distal end of the catheter 31 is located in the interior of the patient's heart according to conventional procedures. The physician then inserts the collapsible heater 30 into the proximal end of the catheter 31 so that the collapsible heater 30 is in the collapsed orientation in which the struts 42 are substantially parallel to each other. This can be accomplished with or without a conventional guidewire. In the case a guidewire is used, a lumen 56 is provided which extends through the cable 41 and through the center electrode 46 of the RF heater. The physician then pushes the cable 41 to force the collapsible heater 30 through the catheter 31 until the collapsible heater 30 is near the distal end of the catheter, as shown in FIG. 5. As the physician continues to push the cable 41, the collapsible heater 30 exits the distal end of the catheter 31 and expands to the deployed orientation as shown in FIG. 3.

When the collapsible heater 30 is positioned at the desired treatment site, the radio-frequency generator 50 is activated to provide suitable energy, preferably at a selected frequency in the range of 10 megahertz to 1000 megahertz, to heat the scar tissue to a temperature sufficient to reduce the surface area of the scar without ablating the scar tissue or damaging the healthy tissue surrounding the infarcted area 12. Preferably, the emitted energy is converted within the scar tissue into heat in the range of about 40 degrees Celsius to about 75 degrees Celsius, more preferably in the range of about 60 degrees Celsius to about 65 degrees Celsius. The radio-frequency energy is preferably applied at low power levels (e.g., 1 to 20 watts). Suitable radio-frequency power sources are readily commercially available. Moreover, the radio-frequency energy can be multiplexed by applying the energy in different patterns over time as appropriate. In one embodiment, the radio-frequency generator 20 has a single channel, delivering approximately 1 to 20 watts of energy and possessing continuous delivery capability. A feedback system can be connected to the collapsible heater 30 for detecting appropriate feedback variables for temperature control. For example, temperature sensing by way of a thermocouple 54 mounted on the distal end of the center electrode 46 may be incorporated to provide feedback to modulate power from the RF generator 50 or other energy source through a feedback loop 56 and/or software within the generator 50 or connector/cable. Alternatively, other feedback systems could be employed, e.g. a thermistor could be mounted to the mylar sheet 52 in a location to contact the infarct scar.

Turning now to FIGS. 6 and 7 other aspects of the present invention are shown. It should be understood that it is important to locate the collapsible heater 30 in close proximity to or touching the infarcted portion 12. It should also be understood that in some cases the infarcted portion 12 is somewhat thinner and weaker than the adjacent, healthy portion of the heart, and consequently when the heart muscles contract the infarcted portion bulges outward from its normal configuration, as indicated in FIG. 6. When this occurs there tends to be blood flow toward the bulge as suggested by arrows 60. Accordingly, the collapsible heater 30 acts like a sail and is carried toward the bulge by the blood flow. Thus the collapsible heater 30 can be said to be self-positioning. It should be understood that to facilitate this self-positioning feature at least the flexible cable 41 and in some cases, both the flexible cable 41 and the catheter 31, must be considerably different from a conventional catheter. Specifically, a conventional catheter is relatively rigid and can include structures to permit a physician to manipulate the distal end of the catheter from a location external to the patient. Such a catheter can be called a "steerable" catheter. In contrast, in the present invention, at least the flexible cable 41 and in some cases, both the flexible cable 41 and the catheter 31 must be quite flexible to allow the blood flow to move the collapsible heater. For this reason, the flexible cable is shown in FIGS. 6 and 7 as somewhat limp, and the catheter 31 can be understood to be a flexible tube, without the components often found in a conventional steerable catheter which to permit a physician to manipulate the distal end of the catheter from a location external to the patient. Similarly, the flexible tube does not include components which permit a physician to manipulate the distal end of the flexible tube from a location external to the patient.

As the heart continues to pump, the collapsible heater is carried toward the infarcted portion 12 until the distal end of the corkscrew-shaped connector 74 contacts the infarct. Then the physician can rotate the handle 76 to rotate the connector so that the connector engages the infarct and pulls the collapsible heater into contact with the infarct, shown in FIG. 7. Then when the physician applies RF energy to the heater 30 the energy is applied directly to the infarct and is not dissipated into blood between the heater 30 and the infarct 12 as would be the case if the heater 30 were spaced apart from the infarct 12. When the procedure is complete, the physician rotates the handle 76 to release the connector 74 from the infarct 12.

Turning now to FIGS. 7a and 7b another embodiment is shown. The embodiment of FIGS. 7a and 7b comprises a heater locating system 110 which comprises a heater 112 which is similar to the collapsible heater 30, except that the heater 112 includes an ultrasonic crystal 114 mounted at the distal end of the center electrode 46. The heater locating system 110 further comprises a locating device 116 including an ultrasonic crystal array which is located outside the patient 106 and which allows a physician to determine the location of the ultrasonic crystal 114. The system of FIGS. 7a-7b further includes a steerable catheter 120, and the heater 112 is mounted to the distal end of the steerable catheter 120. In operation, the heater 112 is introduced into the patient's heart in the same way as is the collapsible heater 30 as discussed above. The physician uses the locating device 116 to monitor the location of the ultrasonic crystal and the heater 112, and the physician uses the steerable catheter 120 to locate the heater adjacent the infarct 12. Then the physician uses the heater 112 to heat the infarct scar in the same way as the collapsible heater 30 as discussed above and illustrated in FIGS. 6 and 7.

It should be understood that other types of monitoring and locating systems could be used by a physician to monitor the location of a heater and locate the heater adjacent an infarct scar.

Figure 8:
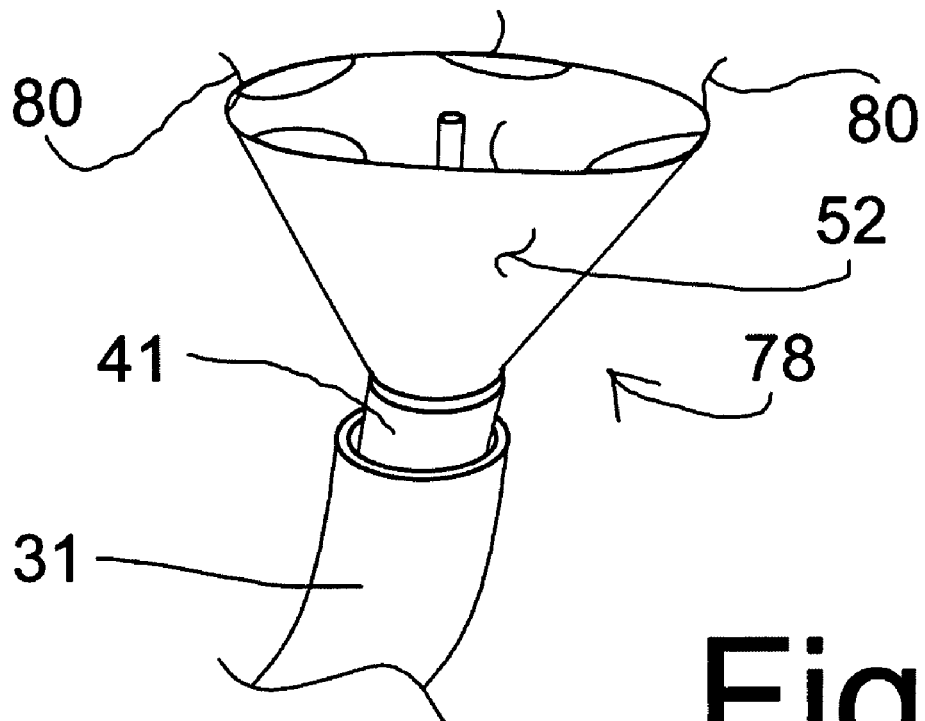
FIG. 8 is an alternative embodiment of the present invention.
Figure 9:
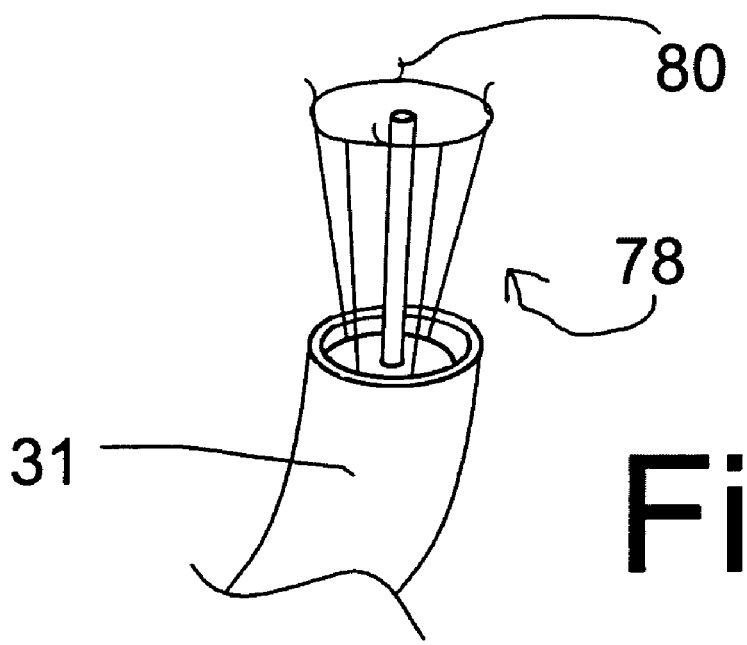
FIG. 9 is a view of the embodiment of FIG. 8 with the mylar removed.
Figure 10:
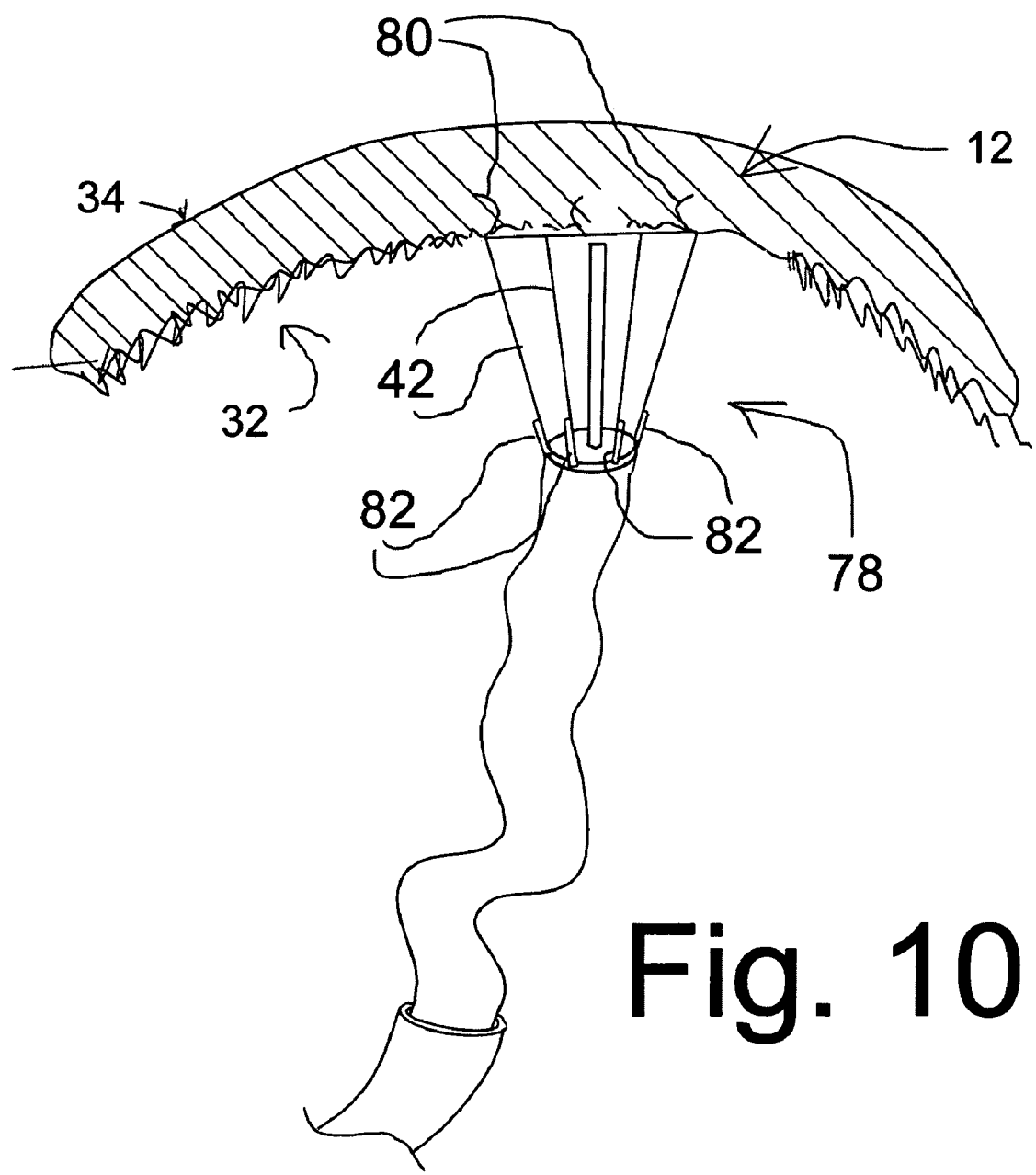
FIG. 10 is a view of another embodiment with part not shown to illustrate internal components.

FIGS. 8-10 show another embodiment which includes an alternative means to connect a heater 78 to the infarct 12. In this embodiment, the heater 78 is similar to heater 30 in most respects, except that in heater 78 the attachment member 70 is absent, instead a plurality of hooks 80 are disposed around the periphery of the wire 44. The hooks 80 are concave with their middle portions being closer to central axis of the heater 30 than their top and bottom portions. In operation, the collapsible heater 78 with hooks 80 is pushed through the catheter 31 until it nears the distal end of the catheter. At this point the distal end of the catheter 31 is positioned adjacent the infarct. Then as the collapsible heater exits the distal end of the catheter 31, as shown in FIG. 9 the struts 31 begin to move away from their collapsed orientation and the hooks 80 engage the infarct as shown in FIG. 10. The physician then heats the infarct as explained above. Thereafter, when heating has been completed, the hooks 80 are released from the infarct 12 by sliding the distal end of the catheter over the struts 42, which causes the hooks 80 to disengage from the infarct 12 to allow removal of the collapsible heater from the heart.

Optionally, as shown in FIG. 10, in heater 78 strain gauges 82 are connected to the struts 42 and the ring 40 to measure flexion of the struts relative to the ring 40, and signals from the strain gauges are carried by wires, not shown, to a meter 84 located outside the patient. (In FIG. 10 the mylar sheet 52 is not shown, in order to illustrate internal components.) This permits measurement of the extent to which the infarcted portion has been treated. Specifically, when the hooks 80 are affixed to infarcted portion the strain measured by the strain gauge 82 is recorded. Then when heat is applied to the infarcted portion 12 the infarcted portion shrinks which causes the distal ends of struts 42 to be drawn toward each other, which in turn causes a change in the strain measured by the strain gauges 82. When the measured strain stops changing it is known that the infarcted portion is completely treated and will not shrink further. At this time heating is discontinued and the heater 78 is removed.

Figure 11:
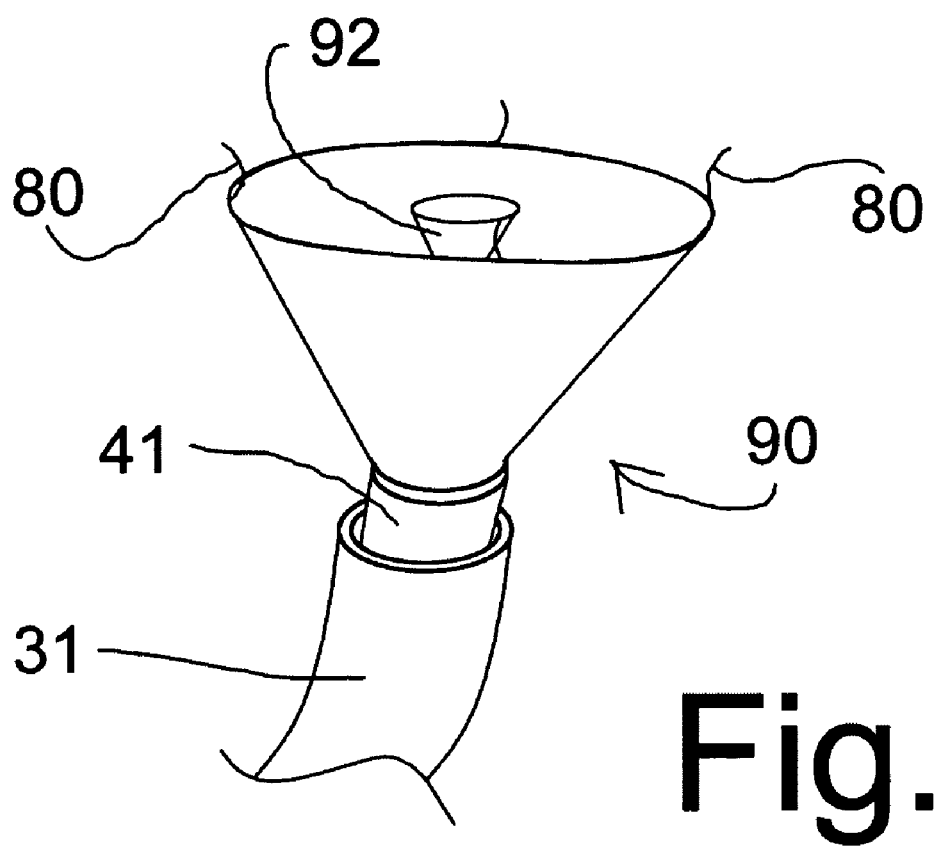
FIG. 11 is a view of another embodiment.

Turning now to FIG. 11 one example of an alternative heater is shown. According to the embodiment shown in FIG. 11 a collapsible heater 90 is similar to heater 78 in most respects, except that in heater 90 there are no center electrode 46 or outside electrodes 48. Rather, there is an infrared light source 92 which is connected to a controllable power supply, not shown, to heat the infarct region.

Figure 12:
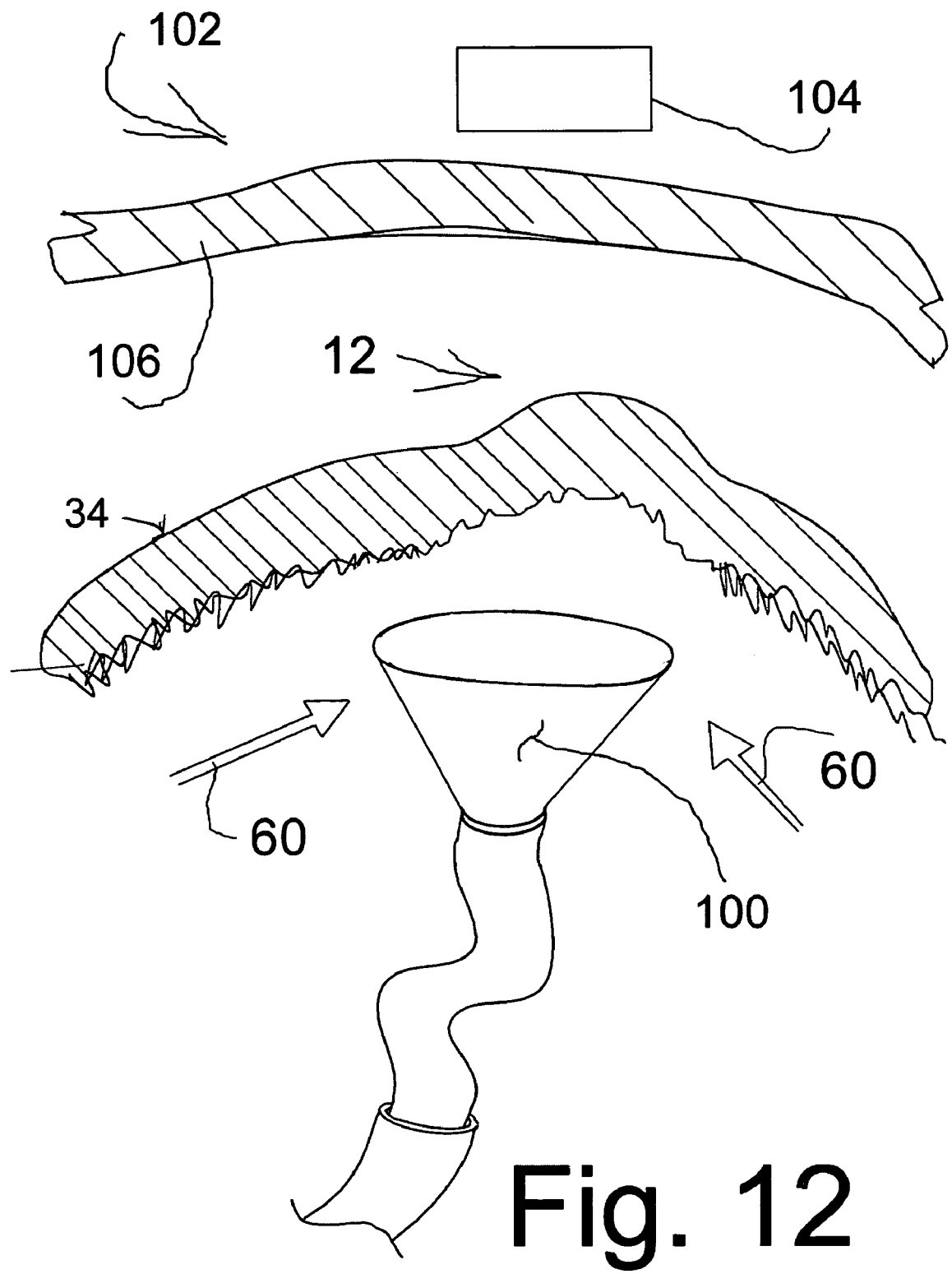
FIG. 12 is a view of still another embodiment, shown with a portion of a patient to illustrate operation of the device.

Turning now to FIG. 12 another embodiment is shown. It should be understood that in the embodiments discussed above, the self-locating aspect of the invention is applied to locating a heater. On the other hand, in the embodiment of FIG. 12 the self-locating feature is not employed to locate a heater but is employed to locate the infarct 12 for other purposes. In certain medical procedures it is important for a physician to be able to accurately locate an infracted region of the heart. One example is to perform electro physiologic ablation using a conventional device. Accordingly, the embodiment of FIG. 12 comprises an infarct locator 100 which is similar to the collapsible heater 30, except that the infarct locator 100 does not include heating elements, and the infarct locating system 102 comprises an acoustic imaging device 104 which is located outside the patient 106 and which allows a physician to determine the location of the infarct locator 100. In operation, the infarct locator 100 is introduced into the patient's heart in the same way as is the collapsible heater 30 as discussed above. Then the infarct locator is located adjacent the infarct 12 by its self-positioning features in the same way as is the collapsible heater 30 as discussed above and illustrated in FIGS. 6 and 7. The physician can use the acoustic imaging device 104 to monitor the location of the infarct locator 100, or other means such as X-ray imaging can be used.

Turning now to FIG. 13 another embodiment is shown. This embodiment is similar to the embodiment shown in FIGS. 3-7. However, the FIG. 13 embodiment includes a system to assist in locating the infarct scar by measuring certain electrical properties of the heart tissue. It should be understood that an infarct scar has resistivity which is greater than that of normal heart muscle and conversely the conductivity of the infarct scar is less than that of normal heart muscle. Moreover, whereas normal heart muscle generates electrical signals, an infarct scar generates no electrical signals. Accordingly, the device of FIG. 13 measures electrical properties of the heart tissue to determine the conductivity, the resistivity or the electrical signals generated by the tissue to thereby ascertain whether the tissue is normal or an infarct scar. To accomplish this a conventional electrical monitoring system 130 is connected to the center electrode 46 and to the outside electrodes 48, and the electrodes 46 and 48 are used are used to transduce electrical signals as necessary.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. A device for treating an infarct scar in a heart, comprising:
   a catheter;
   a collapsible heater connected to said catheter, the collapsible heater including a center electrode and an outer electrode positioned adjacent to the center electrode, wherein the center electrode and outer electrode are positionable within an interior of the heart;
   means for energizing at least one of the electrodes of the collapsible heater to raise the temperature of the infarct scar; and
   a feedback system to enable a user to determine the extent to which heating of the scar has been completed wherein said collapsible heater comprises struts and said feedback system comprises strain gauges connected to said struts.

2. A device according to claim 1 wherein said collapsible heater is connected to a distal end of a cable.

3. A device according to claim 2 wherein said cable is slideable in a lumen of said catheter.

4. A device according to claim 1 wherein said collapsible heater is configured to be slideable through the lumen of said catheter when in a collapsed state.

5. A device according to claim 1 wherein said collapsible heater is constructed to expand to a deployed state in which said collapsible heater occupies greater volume than when said collapsible heater is in a collapsed state.

6. A device according to claim 1 wherein said collapsible heater further comprises:
   a support connected to said catheter;
   a plurality of struts connected to said support;
   a wire coupled to the struts and having a circular configuration surrounding the center electrode;
   a mylar sheet connected to said struts; and,
   a plurality of the outer electrodes connected to the wire.

7. A device according to claim 1, wherein said collapsible heater is a self-positioning heater and comprises a flexible cable connected to said catheter.

8. A device according to claim 1 wherein the heating element raises the temperature of the infarct scar to a temperature sufficient to reduce the surface area of the infarct scar.

9. A device according to claim 1 wherein the center electrode is coupled to a radio frequency generator.

10. A device according to claim 9, wherein the center electrode is a corkscrew shape connector configured to be inserted into the heart tissue.

11. A deviceaccording to claim 9, wherein the heater is a substantially circular electrode on a distal end of said collapsible heater.

12. A device according to claim 1, further comprising a temperature sensor coupled to the heater and configured to be in contact with heart tissue to sense a temperature of the heart tissue.

13. A device according to claim 1, further comprising a hook extending from a periphery of the collapsible heater, wherein the hook is configured to be inserted into heart tissue when the collapsible heater is in a deployed state.

14. A device for treating an infarct scar in a heart, comprising:
   a catheter;
   a center electrode coupled to the catheter;
   a circular electrode coupled to the catheter and configured to be operated between a deployed state and a collapsed state, wherein the electrode is adapted to be slidably moved in a lumen of the catheter in the collapsed state and adapted to be in the deployed state and have an outer conical shape with respect to the center electrode such that the circular electrode is capable of being in contact with heart tissue to treat the infarct scar in the deployed state, the circular electrode having a plurality of hooks extending from periphery of the outer conical shape wherein the hooks are configured to be inserted into heart tissue to secure the circular electrode in contact therewith; and
   a radio frequency generator coupled to at least one of the electrodes and configured to energize the at least one electrode, wherein the center electrode is configured to heat the heart tissue to a desired temperature when energized to reduce the size of the infarct scar.

15. A device for treating an infarct scar in a heart, comprising:
   a catheter;
   a collapsible heater connected to said catheter, the collapsible heater having a strut moveable with respect to the catheter;

means for energizing at least a portion of the collapsible heater to raise the temperature of the infarct scar to shrink the infarct scar; and a feedback system including a strain gauge coupled to the strut, wherein the feedback system is configured to enable a user to determine an amount of shrinkage of the infarct scar from a measurement of the strain gauge.

* * * * *